United States Patent
Kastrup et al.

(10) Patent No.: US 12,226,520 B2
(45) Date of Patent: *Feb. 18, 2025

(54) SELF-FUELED PARTICLES FOR PROPULSION THROUGH FLOWING AQUEOUS FLUIDS

(71) Applicants: The University of British Columbia, Vancouver (CA); The General Hospital Corporation, Boston, MA (US)

(72) Inventors: Christian Kastrup, Vancouver (CA); Ju Hun Yeon, Seoul (KR); James Baylis, Vancouver (CA); Thomas Frederick Burke, Medford, MA (US)

(73) Assignees: The University of British Columbia, Vancouver (CA); The General Hospital Corporation, Boston, MA (US)

( * ) Notice: Subject to any disclaimer, the term of this patent is extended or adjusted under 35 U.S.C. 154(b) by 14 days.

This patent is subject to a terminal disclaimer.

(21) Appl. No.: 17/687,364

(22) Filed: Mar. 4, 2022

(65) Prior Publication Data
US 2022/0233432 A1 Jul. 28, 2022

Related U.S. Application Data

(60) Continuation of application No. 16/295,819, filed on Mar. 7, 2019, now Pat. No. 11,266,596, which is a division of application No. 15/105,553, filed as application No. PCT/CA2014/000721 on Oct. 2, 2014, now Pat. No. 10,238,598.

(60) Provisional application No. 61/916,674, filed on Dec. 16, 2013.

(51) Int. Cl.
| | |
|---|---|
| A61K 9/46 | (2006.01) |
| A61K 9/14 | (2006.01) |
| A61K 9/16 | (2006.01) |
| A61K 38/18 | (2006.01) |
| A61K 38/48 | (2006.01) |
| A61L 15/18 | (2006.01) |
| A61L 15/20 | (2006.01) |
| A61L 15/42 | (2006.01) |
| A61L 15/44 | (2006.01) |
| A61L 29/08 | (2006.01) |
| A61L 29/10 | (2006.01) |
| A61L 29/14 | (2006.01) |
| A61L 29/16 | (2006.01) |
| A61L 31/08 | (2006.01) |
| A61L 31/14 | (2006.01) |
| A61L 31/16 | (2006.01) |
| C01F 11/18 | (2006.01) |

(52) U.S. Cl.
CPC ............ *A61K 9/0007* (2013.01); *A61K 9/143* (2013.01); *A61K 9/145* (2013.01); *A61K 9/1617* (2013.01); *A61K 38/18* (2013.01); *A61K 38/4833* (2013.01); *A61L 15/18* (2013.01); *A61L 15/20* (2013.01); *A61L 15/425* (2013.01); *A61L 15/44* (2013.01); *A61L 29/08* (2013.01); *A61L 29/10* (2013.01); *A61L 29/106* (2013.01); *A61L 29/146* (2013.01); *A61L 29/16* (2013.01); *A61L 31/08* (2013.01); *A61L 31/082* (2013.01); *A61L 31/088* (2013.01); *A61L 31/146* (2013.01); *A61L 31/16* (2013.01); *C01F 11/18* (2013.01); *A61L 2300/254* (2013.01); *A61L 2300/418* (2013.01); *A61L 2300/606* (2013.01); *A61L 2400/04* (2013.01); *A61L 2400/12* (2013.01); *A61L 2420/06* (2013.01); *C01P 2004/61* (2013.01); *C01P 2006/16* (2013.01); *C12Y 304/21005* (2013.01)

(58) Field of Classification Search
CPC ...... A61K 9/0007; A61K 9/143; A61K 9/145; A61P 7/04
See application file for complete search history.

(56) References Cited

U.S. PATENT DOCUMENTS

| | | | |
|---|---|---|---|
| 3,939,289 A | | 2/1976 | Hornyak et al. |
| 4,465,662 A | * | 8/1984 | Sato ...................... A61Q 11/00 424/48 |
| 5,209,251 A | | 5/1993 | Curtis et al. |
| 5,779,464 A | | 7/1998 | Fan et al. |
| 5,792,473 A | | 8/1998 | Gergely et al. |

(Continued)

FOREIGN PATENT DOCUMENTS

| | | |
|---|---|---|
| CA | 2 339 836 C | 3/2000 |
| CA | 2 363 916 A1 | 7/2000 |

(Continued)

OTHER PUBLICATIONS

Lambros et al (Pharmaceutics, 2022, vol. 14, pp. 1-18) (Year: 2022).*

(Continued)

*Primary Examiner* — Mark V Stevens
(74) *Attorney, Agent, or Firm* — Christensen O'Connor Johnson Kindness PLLC

(57) ABSTRACT

A simple, self-propelling particle system is disclosed that can deliver a cargo through flowing aqueous solutions. This disclosure provides a non-aqueous composition comprising: (i) particles formed of a carbonate salt and having an average diameter of about 100 μm or less; and (ii) an acid in solid form. The particles may be associated with a cargo molecule or particle. In mouse models of severe hemorrhage, the propelled particles are able to deliver a procoagulant enzyme and halt bleeding.

15 Claims, 7 Drawing Sheets

(56) References Cited

U.S. PATENT DOCUMENTS

| | | | |
|---|---|---|---|
| 5,951,531 | A | 9/1999 | Ferdman et al. |
| 6,225,123 | B1 | 5/2001 | Cohen et al. |
| 6,368,298 | B1 | 4/2002 | Beretta et al. |
| 6,534,016 | B1 | 3/2003 | Cohen et al. |
| 10,238,598 | B2 | 3/2019 | Kastrup et al. |
| 2003/0031632 | A1 | 2/2003 | Kiji et al. |
| 2005/0175675 | A1 | 8/2005 | Seibertz |
| 2006/0188562 | A1 | 8/2006 | Gower et al. |
| 2008/0038311 | A1 | 2/2008 | Vogt et al. |
| 2008/0160051 | A1 | 7/2008 | Sirota |
| 2011/0066182 | A1 | 3/2011 | Falus |
| 2012/0004636 | A1* | 1/2012 | Lo .................. A61L 15/44 206/440 |
| 2015/0283082 | A1 | 10/2015 | Gerard et al. |
| 2016/0354315 | A1 | 12/2016 | Li |
| 2018/0116911 | A1 | 5/2018 | Li |

FOREIGN PATENT DOCUMENTS

| | | | |
|---|---|---|---|
| CA | 2 449 436 A1 | 1/2003 | |
| CA | 2 599 929 A1 | 3/2008 | |
| EP | 1 919 859 B1 | 6/2010 | |
| EP | 2695605 A1 | 2/2014 | |
| EP | 2 719 373 A1 | 4/2014 | |
| GB | 883169 A * | 11/1961 | |
| JP | 3894110 B2 | 3/2007 | |
| WO | 2005/016257 A2 | 2/2005 | |
| WO | WO-2011083154 A1 * | 7/2011 | ........... A61K 38/363 |
| WO | 2013/004838 A1 | 1/2013 | |
| WO | 2015089626 A1 | 6/2015 | |

OTHER PUBLICATIONS

Kimura et al (Hypertension, 2004, vol. 44, pp. 969-973) (Year: 2004).*

Fantl.(Biochimica et Biophysica Acta (BBA)—General Subjects, 1966, vol. 130, pp. 87-91) (Year: 1966).*

Office Action mailed Aug. 18, 2022, issued in corresponding Canadian Application No. 2,937,049, filed Oct. 2, 2014, 4 pages.

Baylis, J., et al., "Self-Propelling Particles That Transport Cargo Through Flowing Blood and Halt Hemorrhage," Norman Bethune Poster, Apr. 2014, 1 page.

Baylis, J., et al., "Self-Propelling Particles That Clot Blood and Halt Hemorrhaging," Poster from CAN-MNCH Meeting, Oct. 3, 2013, 1 page.

Baylis, J., et al., "Self-Propelling Particles That Clot Blood and Halt Haemorrhaging," Poster from US-Japan Meeting, Dec. 2013, 1 page.

Baylis, J., et al., "Self-Propelled Particles That Transport Cargo Through Flowing Blood and Halt Hemorrhage," Science Advances 9:e1500379, 2015, 8 pages.

Baylis, J., "Self-Propelled Particles That Clot Blood and Halt Haemorrhage," Slide Show, Vancouver Nanomedicine Day, Vancouver, B.C., Canada, May 5, 2014, 21 pages.

"CYKLOKAPRON®," Pfizer Injectables, [Author Unknown], Jan. 2011, 6 pages.

Dreyfus, R., et al., "Microscopic Artificial Swimmers," Nature 437(7060):862-865, Oct. 2005.

Extended European Search Report and Opinion, mailed May 16, 2017, for EP Application No. 14871728.3, 8 pages.

Garcia-Gradilla, V., et al., "Functionalized Ultrasound-Propelled Magnetically Guided Nanomotors: Toward Practical Biomedical Applications," ACS Nano 7(10):9232-9240, Oct. 2013.

International Search Report of the ISA, mailed Jan. 9, 2015, for International Application No. PCT/CA2014/000721, 5 pages.

International Preliminary Report on Patentability of the ISA, mailed Jun. 21, 2016, for International Application No. PCT/CA2014/000721, 7 pages.

Smagilov, R.F., et al., "Autonomous Movement and Self-Assembly," Angewandte Chemie International Edition 41(4):652-654, 2002.

Kastrup, C., "Polymers, Self-Propelling Particles and Other Short Stories About Blood Clots," Slide Show at Simon Fraser University, Mar. 7, 2014, 17 pages.

Kastrup, C., "Clotting the Unclottable: Halting Severe Hemorrhaging, and Clotting Without Fibrinogen," Slide Show, Nov. 14, 2013, University of British Columbia, Vancouver, B.C., Canada, 8 pages.

Kastrup, C., "UBC Inventor of Self-Propelled Coagulant Wins Grant From Grand Challenges Canada," Nov. 23, 2012, University of British Columbia Faculty of Medicine, <http://www.med.ubc.ca/ubc-inventor-of-self-propelled-coagulant-wins-grant-from-grand-challenges-canada/> [retrieved Oct. 31, 2017], 2 pages.

Kawai, K., et al., "Calcium-Based Nanoparticles Accelerate Skin Wound Healing," PloS One 6(11):e27106, Nov. 2011, 13 pages.

Khalil, I.S.M., et al., "Magnetic Control of Potential Microrobotic Drug Delivery Systems: Nanoparticles, Magnetotactic Bacteria and Self-Propelled Microjets," Engineering in Medicine and Biology Society (EMBC), 35th Annual International Conference of the IEEE, Jul. 2013, pp. 5299-5302.

Kuralay, F., et al., "Self-Propelled Carbohydrate-Sensitive Microtransporters With Built-In Boronic Acid Recognition for Isolating Sugars and Cells," Journal of the American Chemical Society 134(37):15217-15220, Sep. 2012.

Niego, B., et al., "Desmoteplase-Mediated Plasminogen Activation and Clot Lysis are Inhibited by the Lysine Analogue Tranexamic Acid," Blood Coagulation & Fibrinolysis 19(4):322-324, Jun. 2008.

Patra, D., et al., "Intelligent, Self-Powered, Drug Delivery Systems," Nanoscale 5(4):1273-1283, Jan. 2013.

Paxton, W.F., et al., "Chemical Locomotion," Angewandte Chemie International Edition 45(33):5420-5429, Aug. 2000.

Petrov, A.I., et al., "Protein-Calcium Carbonate Coprecipitation: A Tool for Protein Encapsulation," Biotechnology Progress 21(3):918-925, May-Jun. 2005.

Preisig, D., et al., "Drug Loading Into Porous Calcium Carbonate Microparticles by Solvent Evaporation," European Journal of Pharmaceutics and Biopharmaceutics 87(3):548-558, Aug. 2014.

Senthong, A., and S. Taneepanichskul, "The Effect of Tranexamic Acid for Treatment Irregular Uterine Bleeding Secondary to DMPA Use," Journal of the Medical Association of Thailand 92(4):461-465, 2009; abstract.

Sukhorukov, G.B., et al., "Porous Calcium Carbonate Microparticles as Templates for Encapsulation of Bioactive Compounds," Journal of Materials Chemistry 14(14):2073-2081, 2004.

Jeno, Y., et al., "Drug-Incorporating Calcum Carbonate Nanoparticles for a New Delivery System," Journal of Controlled Release 103(1):93-98, Mar. 2005.

Volodkin, D.V., et al., "Protein Encapsulation via Porous $CaCO_3$ Microparticles Templating," Biomacromolecules 5(5):1962-1972, Sep.-Oct. 2004.

Written Opinion of the ISA, mailed Jan. 9, 2015, for International Application No. PCT/CA2014/000721, 6 pages.

Wu, Z., et al., "Self-Propelled Polymer-Based Multilayer Nanorockets for Transportation and Drug Release," Angewandte Chemie International Edition 52(27):7000-7003, Jul. 2013.

Zhao, G., et al., "Challenges of the Movement of Catalytic Micromotors in Blood," Lab on a Chip 13(10):1930-1936, May 2013.

Canadian Examination Report mailed Oct. 29, 2020, issued in corresponding Canadian Application No. 2,937,049, filed Oct. 2, 2014, 4 pages.

Salim G., P., et al., "Formulation and Evaluation of Effervescent Tablets: A Review," Journal of Drug Delivery & Therapeutics 8(6):296-303, 2018.

Office Action mailed Mar. 20, 2023, issued in corresponding Canadian Application No. 2,937,049, filed Oct. 2, 2014, 3 pages.

* cited by examiner

SELF-FUELED PARTICLES FOR PROPULSION THROUGH FLOWING AQUEOUS FLUIDS

RELATED APPLICATIONS

This application is a continuation of U.S. application Ser. No. 17/687,364 filed Mar. 4, 2022, which is a division of U.S. application Ser. No. 16/295,819 filed Mar. 7, 2019, which is the national stage of U.S. application Ser. No. 15/105,553 filed Jun. 16, 2016, which claims priority from PCT/CA2014/000721 filed Oct. 2, 2014, which claims the benefit of U.S. Application No. 61/916,674 filed Dec. 16, 2013, each application expressly incorporated herein by reference in its entirety.

FIELD OF THE INVENTION

This invention relates to particles capable of self-propulsion.

BACKGROUND

Uncontrolled bleeding occurs in many situations, including severe nosebleeds, post-partum hemorrhage (PPH), trauma, dental procedures, and bleeding in patients with hemophilia. The primary concern during severe bleeding is quickly controlling blood loss, although controlling secondary bleeding, infection, and tissue repair is also important. Delivery of appropriate therapeutics, such as coagulants, anti-fibrinolytics, antimicrobials, or growth factors to the damaged vasculature can help. However, delivering such agents via systemic injections or via intravascular catheter is often not possible, particularly if the person is far from an advanced clinical setting. Topical delivery is limited by the difficult biophysical problem of moving agents upstream through blood flow and deep enough into an area of bleeding where they could treat the leaking vessels. Severe hemorrhaging is often fatal because coagulants are not able to reach and clot blood at the level of damaged vessels.

Propelled particle systems have been previously proposed for drug delivery.[1-6] Some of these particles rely on gas generation and bubble propulsion to create their velocity. Such particles may contain metal catalysts that convert hydrogen peroxide dissolved in aqueous solution to oxygen gas. Other examples convert hydrogen ions in strongly acidic solutions (pH<1) to a hydrogen gas. Thus, the "fuel" for propulsion or a necessary reactant is placed in the environment of the particle and is not present in the particle itself. Mechanisms such as ultrasound or magnetically-driven swimmers for propulsion have also been proposed.[7,8]

Particles that employ gas/bubble propulsion have not been used in vivo because they rely on having a "fuel" (e.g., hydrogen peroxide) which is toxic or a required reactant (i.e., a strong acid) dispersed in the living environment. Also, they generally propel at velocities many orders of magnitude slower than blood flow.[1,4] Despite drawbacks with regard to in vivo use, progress has been made in the design of particles generally capable of functioning as microjet engines or "rockets" such as rolled microtubes, including conical versions of microtubes[3,5,12]. Polymer components and/or layers in such particles may be adapted for carrying drugs as well as for insulating a carrier from a reactant or "fuel" such as hydrogen peroxide, until such time as a barrier layer dissolves.

Independent from development of propelled particles are the advances that have been made in drug microcarriers. Various microparticles are known for use in carrying biologically active substances to enhance delivery to target cells, tissues, etc. Microparticles, including porous versions thereof that are made of polyelectrolytes and are capable of adsorption of biologically active materials have, been developed for drug delivery. Examples of such particles have been made by crystallizing inorganic salts such as calcium carbonate. Also, processes for controlled fabrication of films and particles have been developed, including ones which allow for precise control of film or particle shell thickness (i.e., nanoporous template-assisted layer-by-layer (ELbL) protocols).

Volodkin et al.[9] describe production of porous $CaCO_3$ (vaterite) particles with a size distribution from 4 to 6 µm that encapsulate proteins that are adsorbed to the particles. Such particles were found to be biocompatible and decomposable at neutral pH.

Compositions comprising metal carbonates and organic acids that effervesce in contact with aqueous media have been disclosed as additives for collection devices containing bodily fluids (U.S. Pat. No. 6,225,123). The latter Patent teaches that such compositions may include a clot activator such as silica particles. The effervescence will assist in distributing the clot activator throughout a collection vessel to promote rapid blood coagulation prior to removal of serum. Such additives can be made in solid forms (including tablets) for addition to tubes containing blood samples.

It is known that the presence of calcium ions in a wound bed will promote healing and this has led to treatments involving topical application of calcium to wounds, such as through use of calcium alginate dressings. Kawai et al.[13] prepared 50-200 nm nanoparticles from collagen and calcium chloride for intravenous injection. They found better wound healing in an open wound mouse model after injection of the calcium-based nanoparticles as compared to intravenous injection of calcium chloride. They also compared results following topical administration of calcium chloride and calcium-based nanoparticles directly to open wounds. Consistent with results obtained with calcium containing dressings, topical administration of calcium chloride accelerated healing but topical administration of the calcium-based nanoparticles did not significantly change wound healing rate.

Foaming hemostatic and adhesive fibrin preparations that may contain calcium ions are also known, such as those disclosed in WO2000/038752 and WO2011/123346. Spreading of components that provide for a fibrin matrix results from the foaming action. The foaming results from generation of $CO_2$. Neither reference discloses particles that propel themselves. For example, WO2011/123346 discloses the generation of $CO_2$ by mixing a solution containing fibrin scaffold components and sodium bicarbonate with an acidic solution. WO2000/038752 discloses a composition in powder or granular form that contains components for forming a fibrin matrix, together with a carbonate and a physiologically acceptable organic acid. The latter composition effervesces upon contacting moisture.

SUMMARY

The present disclosure is of a simple, self-propelling particle system that can deliver a cargo through flowing aqueous solutions. This system is functional, and in a mouse model of severe hemorrhage the propelled particles are able to deliver a procoagulant enzyme and halt bleeding. This system has application for the delivery of cargo through flowing aqueous fluids. In particular embodiments, the fluid will be flowing at a rate of less than about 5, 4, 3, 2, or 1 mm/s. Compositions of this invention may be useful for delivery of therapeutics to sites of injury or hemorrhage or in treating external bleeding that originates from inside the body, such as the uterus, naval cavity, or abdominal cavity, where traditional topical agents are not particularly effective.

This disclosure is based at least in part, on the discovery that self-fueled particles can generate sufficient energy to propel themselves against the flow of a moving fluid, including flowing blood. Such particles may be used for local delivery of biologically active agents including delivery which allows for movement of the particles into areas of bleeding. Furthermore, the particles themselves may be designed to assist in blood clotting and/or wound healing.

This disclosure relates to a method of conveying a cargo molecule or cargo particle through an aqueous fluid, the method comprising providing a self-fueled particle associated with said cargo molecule or particle, the self-fueled particle comprising a fuel for releasing gas to propel the particle when contacted with the aqueous fluid. The particles may be formed of a carbonate salt as described herein.

This disclosure also relates to compositions comprising solid particles that comprise a carbonate salt; and, an acid, in solid form, in admixture or distributed in or on a non-aqueous matrix, support or carrier. Particular embodiments involve a non-aqueous composition comprising: (i) particles formed of a carbonate salt and having an average diameter of about 100 μm or less; and (ii) an acid in solid form. In some embodiments, the composition consists essentially of the acid in solid form and the particles formed of a carbonate salt, with or without an associated cargo.

The carbonate salt containing particles may be associated with a cargo particle or a cargo molecule, which may be a biologically active agent. Thus, this invention also relates to a method of conveying a cargo molecule or particle through a flowing aqueous fluid using such a composition that is introduced into the fluid. The fluid may be a bodily fluid.

This disclosure also relates to use of a composition as described herein for delivery of a biological agent through a bodily fluid. The bodily fluid may be flowing. Such use may be for treatment of bleeding. A composition as described herein may be for administration locally, including to an area of bleeding. A composition as described herein may be adapted for topical administration or placement directly on an area bleeding during surgical treatment.

This disclosure also relates to $CaCO_3$ nanoparticles and/or microparticles that are associated with a biological agent capable of affecting clotting, including agents that promote clotting such as thrombin, tissue factor and other procoagulants or anti-fibrinolytics. Alternatively, the agent may be one that diminishes clots or clotting such as tissue plasminogen activator (tPA).

This disclosure also relates to non-aqueous compositions comprising $CaCO_3$ nanoparticles and/or microparticles and the organic acid $THX-NH_3^+$. The particles may be associated with a cargo molecule or particle as described herein. The composition may consist essentially of the acid and the particles, with or without associated cargo.

$CaCO_3$ particles for use in this invention may be microparticles of a size ranging from about 1 to about 100 μm in average diameter; less than about 50 μm in average diameter; about 20 to about 60 μm in average diameter; 2 to about 10 μm in average diameter; or about 4 to 6 or about 10 μm in average diameter. Nanoparticles having a diameter of less than about 1 μm (e.g. about 0.1 to about 0.5 μm or greater) are also contemplated. The particles may be porous. Pore size in the particles may be in the range of about 10 to about 100 nm, or about 20 to about 60 nm. Such particles may be ones prepared by precipitation of porous vaterite particles from an equimolar solution of $Na_2CO_3$ and $CaCl_2$.

This disclosure also relates to materials, devices and instruments associated with a composition as described herein. For example, the composition may be distributed on or impregnated in materials such as gauze, wound dressings, sponges, nasal packing material, and balloons used in surgical treatment. Such a balloon may be a uterine application. This disclosure also relates to delivery devices including syringes and catheters comprising a composition as described herein and may include other devices such as pumps, distribution apparatus, tubing or the like, not necessarily intended for treatment of a living organism. Compositions of this invention may be employed in microfluidic systems.

DETAILED DESCRIPTION OF THE INVENTION

Figure 1A:
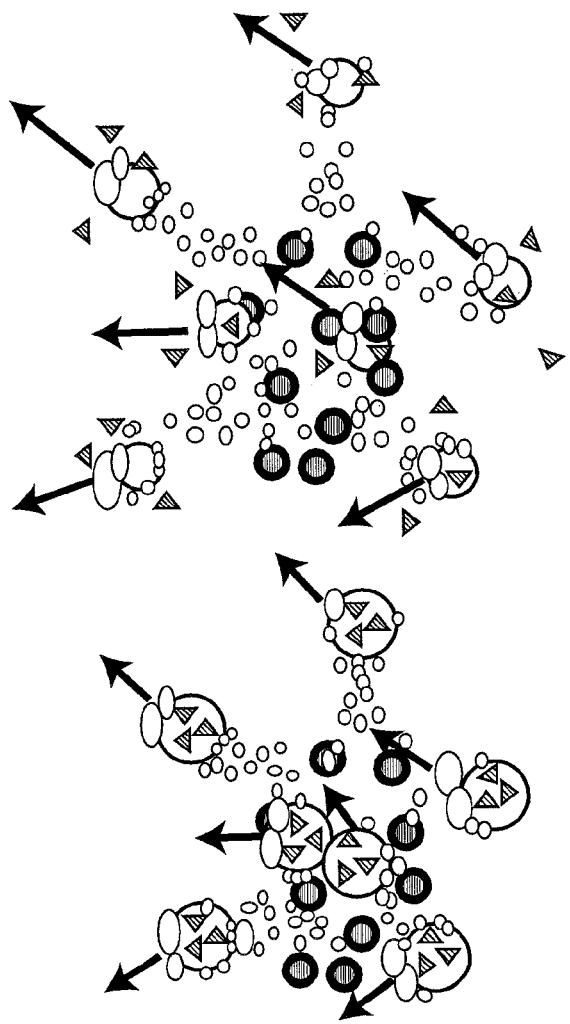
FIG. 1A is a schematic showing $CaCO_3$ microparticles associated with a cargo that propel themselves through aqueous solutions when combined with an organic acid. The 3-component system reacts and $CO_2$ is released from the microparticles when placed in water.

Compositions of this invention comprise a carbonate salt and an acid and are therefore moisture sensitive. The composition should be prepared such that there is minimal opportunity for reaction of the carbonate salt and the acid until the composition is contacted with an aqueous medium. The salts may be physiologically acceptable salts. Examples of carbonate salts that are physiologically acceptable include $CaCO_3$ and $Na_2CO_3$. However, in applications where wound healing is enhanced and particularly in cases where the composition is employed to enhance blood clotting, the preferred salt is $CaCO_3$. The particles may be prepared by any means but in some cases, it can be advantageous to prepare porous particles to increase particle surface area and/or to provide for at least partial encapsulation of a cargo molecule or particle. Methods for producing porous carbonate salt particles are known in the art, such as in the above-described publication of Volodkin et al.[9]

The acid component a composition of this invention may be any acid suitable for preparation of the composition in solid form and/or for the intended use of the composition. For example, the acid may be physiologically acceptable for use in biological systems. Examples of suitable acids include organic acids. Examples of physiologically acceptable organic acids include citric acid and malic acid. However, in applications for promotion of blood clotting, it is desirable that the organic acid not be capable of chelating calcium cations at physiological pH (i.e., from pH 6.5 to 8.0). Amino acids and organic acids derived from amino acids that are not chelators at physiological pH are suitable. These include amino acids that are protonated at physiological pH (e.g., glycine) or which can be protonated in that pH (e.g., tranexamic acid). The latter substance is approved for clinical use as an anti-lytic agent and will enhance blood clotting. Another example of an organic acid derived from an amino acid that enhances blood clotting is aminocaproic acid. However, where the indication requires lysing of blood clots, anti-fibrinolytic agents such as tranexamic acid or aminocaproic acid or procoagulants should be avoided.

Cargo particles or molecules that may be associated with the carbonate salt particles for use in this invention may be any substance that can be so associated. The cargo may be present to act as a label or the cargo may have another function such as a biological function. The term "associated" is meant to include any form of binding, including electrostatic interaction. Polyelectrolytes such as $CaCO_3$ particles are particularly suitable for adsorbing biological material such as proteins, nucleic acids, polysaccharides and other charged substances such as dextrans. The term "associated" is also intended to include physical constraints such as encapsulating or otherwise enclosing an associated substance.

Cargo particles to be associated with the carbonate salt particles for use in this invention should be of a size approximately similar to the carbonate salt particle or smaller. Thus, in, particular embodiments, it is desirable for a cargo particle to be 10 μm or 5 μm or less in size.

Biologically active agents that may be associated as cargo molecules with carbonate salt particles in this invention may be any active macromolecule (such as a protein) or a small molecule that can be so associated and may include, without limitation: growth factors; antimicrobials; antibiotics; styptics; anesthetics; anti-proliferative drugs such as methotrexate and other anti-cancer drugs; procoagulants such as thrombin; anti-fibrinolytic agents; fibrinolytic agents such as urokinase-type plasminogen activator (uPA); antifibrotics such as acetylsalicylic acid (ASA); and anti-inflammatory agents such as dexamethasone.

Carbonate salt particles employed in the invention may be of a size which is not desirable for systemic delivery nor would systemic delivery be recommended if a particular composition of this invention comprises a procoagulant. Nevertheless, compositions of this invention can be suitable for direct application to an area to be treated. Such application includes local administration, topical administration, placement of a composition of this invention on an area during surgical treatment, and the like. Local administration may comprise delivery of a composition of this invention by means of a device such as a catheter to a particular target area. Topical administration may comprise placement of a composition of this invention directly on a wound or area of bleeding. Compositions comprising nonparticles may be useful for systemic administration.

Compositions of this invention may be for use in propelling a cargo through an aqueous fluid that is in motion in virtually any system, including biological systems. Compositions of this invention may be formulated for therapeutic use using known techniques and materials such as is described in texts such as Remington: The Science and Practice of Pharmacy (latest edition). A composition of the present invention may be formulated into therapeutic compositions with appropriate pharmaceutically acceptable carriers or diluents. Preparations may be solid or non-aqueous, semi-solid and liquid forms, such as tablets, capsules, pills, powders, granules, dragées, gels, creams, slurries, ointments, and suspensions.

Compositions of this invention may be present on microcarriers known in the art, including physical microstructures that have been previously employed as self-propelling particles. These include tubular structures, including ones with open ends as well as ones in conical shape having open ends of different diameters. Such microcarriers may also be in the form of a bead, microcapsule, etc. They may be comprised of materials such as glass, metal and/or polymers and may be magnetic and/or labelled. Degradable polymer microspheres are known for use with therapeutic proteins. Microspheres can be prepared from degradable polymers such as poly(lactide-co-glycolide) (PLG), polyanhydrides, poly (ortho esters), non-biodegradable ethylvinyl acetate polymers, in which proteins are entrapped in the polymer (e.g., see: Ranade and Hollinger, "Drug Delivery Systems" (CRC Press 1996).

Compositions of this invention may be associated with another material that has a desirable biological effect, including materials that affect clotting. For example, compositions of this invention may contain or be associated with silica or kaolin based compositions as currently employed for control of hemorrhaging.

Compositions of this invention may be distributed on or within various materials that are employed for therapeutic purposes, including gauze, packing, balloons, etc. Various means may be used for adhering or impregnating a composition of this invention to such materials. In particular embodiments, such material present in the faun of sheets or layers may separately contain the carbonate salt and acid components of a composition of this invention, to assist localization of the components and to minimize reaction prior to application to an area where the material will be wetted by a bodily fluid.

Compositions of this invention and materials comprising such compositions are typically dry but may also be present in a non-aqueous gel or a liquid such as an oil. Preparation of non-aqueous carriers for therapeutic purposes which employ hydrophilic polymers is known in the art. For example, non-aqueous gels for topical delivery of moisture-sensitive drugs are known[14].

This invention also provides kits comprising the carbonate salt and acid components of a composition as defined above, which components are present in separate containers or packaging. Such a kit may include instructions for use of the components for preparation and use of a composition of this invention.

Delivery devices may comprise a composition of this invention. Such devices may be for use in therapeutic administration of a composition of this invention and can include catheter containing apparatus suitable for delivery of a biological agent such as tPA locally to a target area.

Exemplary embodiments of the present invention including ones suitable for treatment of bleeding are described in the following examples.

Examples

To prepare self-propelling particles that would be particularly applicable for treating hemorrhaging, we chose materials that were already approved for clinical use and that can be formulated into a powder that only requires water to produce gas. Calcium carbonate ($CaCO_3$) is a commonly used substance in antacid tablets and drug formulations and rapidly produces gas bubbles of $CO_2$ in acidic solutions. Microparticles of $CaCO_3$ had been prepared previously that are porous and can adsorb protein.[9]

Porous microparticles used in this example can be prepared by precipitation of $CaCO_3$ when $Na_2CO_3$ is added to a solution containing $CaCl_2$, based on the procedure described by Volodkin et al.[9] For example, ice cold 0.33 M $Na_2CO_3$ can be added to an equal volume of ice cold 0.33 M $CaCl_2$ with rapid mixing. The particles can be fluorescently labeled, for example by precipitating the $CaCO_3$ in the presence of 0.1 mg/mL FITC-dextran (4 KDa mw) or with fluorescent polystyrene micro or nanoparticles (such as green-fluorescent microspheres available from Polysciences, Inc. or dark red-fluorescent carboxylate-modified polystyrene nanoparticles available from Life Technologies).

Figure 1B:
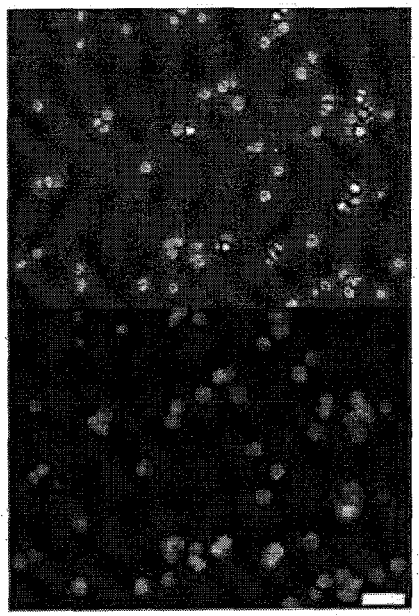
FIG. 1B is an image of immobilized $CaCO_3$ microparticles (10 μm dia.) associated with a fluorescently-tagged cargo molecule, FITC-dextran. Scale bar is 30 μm.

Precipitated $CaCO_3$ particles can be purified by centrifugation, washed with deionized water, and dried (for example at 60° C.). Such particles will generally have spherical geometry and may typically have diameters ranging from about 2 to about 10 μm (FIG. 1B). We found that when such $CaCO_3$ microparticles were mixed with a solid organic acid, they were rapidly propelled though both buffered aqueous solutions and whole blood (FIG. 1A).

In order to convert tranexamic acid (TXA) to its doubly-protonated form (TXA-$NH_3$), 6 M HCl was added to 0.5 M neutrally-charged TXA (TXA-$NH_2$) until pH 4.3. The acidified solution was lyophilized yielding solid TXA-$NH_3^+$.

Figure 1C:
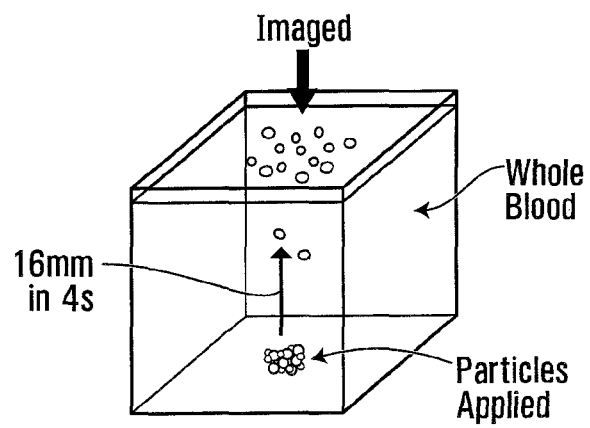
FIG. 1C is a schematic showing how particle propulsion was measured for the results shown in FIGS. 1D and 1E.
Figure 1D:
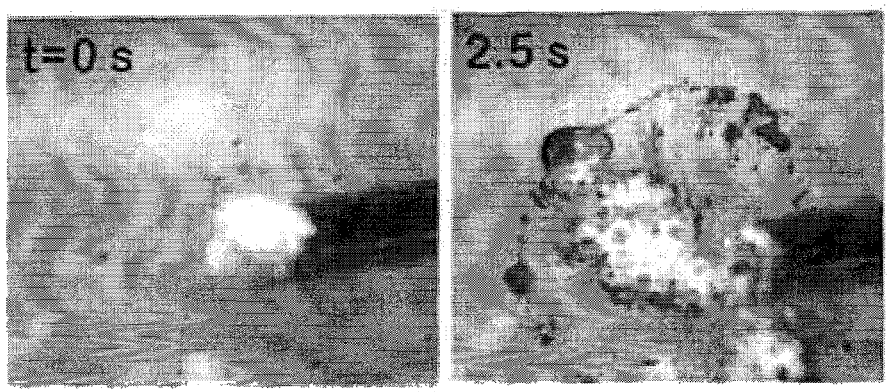
FIGS. 1D and 1E are images of fluorescently-tagged particles appearing at the surface of a buffered solution (D) and blood (E), after propelling from 16 mm below the surface. Scale bar is 2 mm.
Figure 1E:
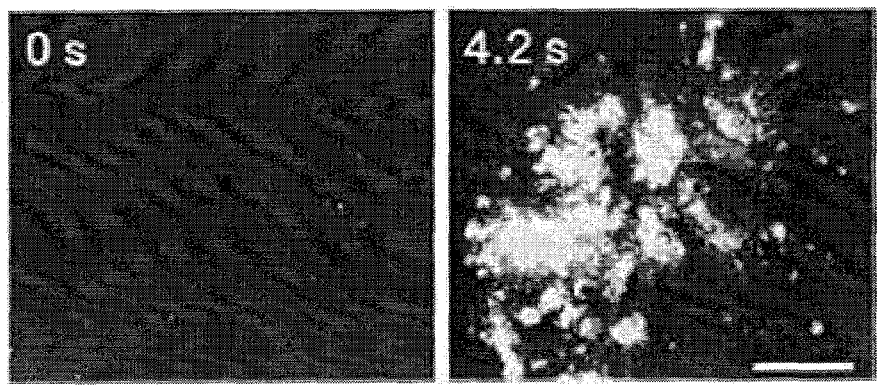

In order to assess propulsion capabilities, $CaCO_3$ microparticles were mixed at approximately 1:1 molar ratio with TXA-$NH_3^+$ and injected directly to phosphate-buffered saline (PBS) or whole blood, 16 mm below the surface via a needle (FIG. 1C). The particles reacted vigorously, rising and spreading at the surface within seconds (FIG. 1D). After the reaction, the pH of the solution was neutral, as the acid was neutralized when $CO_3^{2-}$ protonated and reacted.

When the $CaCO_3$ microparticles were mixed with unprotonated tranexamic acid (TXA-$NH_2$), rather than TXA-$NH_3^+$, the particles did not react or propel. It had recently been suggested that propulsion of particles through whole blood would be unachievable by catalytic microengines.[2] However, the results here show that generating gaseous bubbles can achieve propulsion through blood.

Figure 2A:
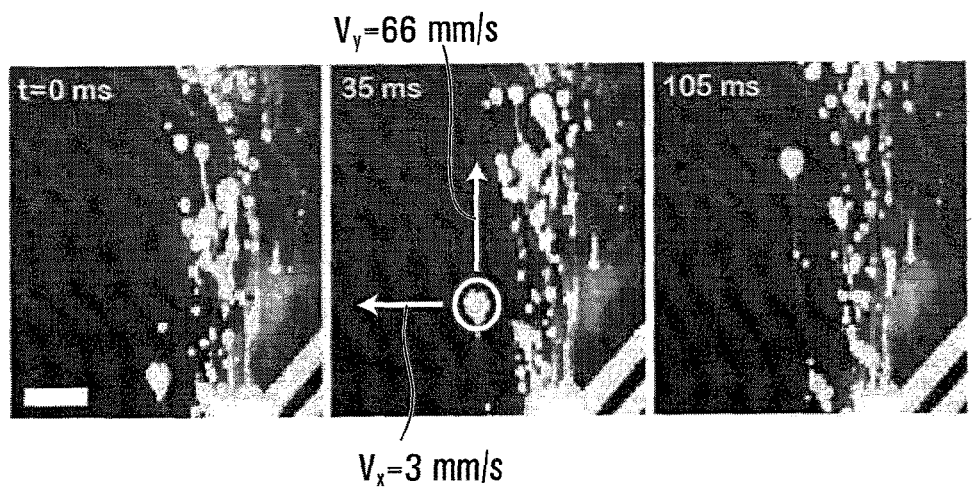
FIG. 2A is a series of images showing $CaCO_3$ particles propelling upstream through a flowing acidic solution over time. The circled particle had vertical and horizontal velocity components of 66 mm/s and 3 mm/s, respectively.
Figure 2B:
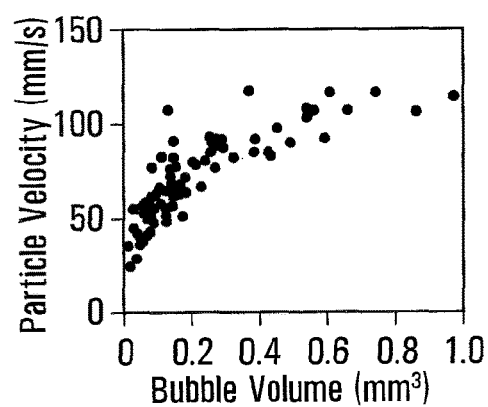
FIG. 2B is a graph showing that particle velocity increases with the volume of bubbles to which the particle is attached.

To illustrate the range of applications in which the $CaCO_3$ particles may be useful, velocity of the particles in both stagnant and flowing solutions was quantified. To simplify the initial analysis, the organic acid (TXA-$NH_2$) was first dissolved in water. $CaCO_3$ microparticles were injected at the bottom of the container and particle trajectories imaged at 35 ms resolution (FIG. 2A). The microparticles usually reacted as aggregates, with a diameter of 0.4±0.16 mm, which broke apart into smaller particles as they reacted and propelled. Particles had upward velocities of 71±23 mm/s and lateral velocities of 3.6±3.5 mm/s. These velocities are among the fastest reported for any self-propelling particles.[1,4] The particle velocity increased as a function of bubble volume (FIG. 2B). We also used this approach to demonstrate upward propulsion of such particles from a gauze impregnated with the $CaCO_3$ microparticles and TXA-$NH_3^+$ placed at the bottom of an inverted tubular container containing water.

Figure 2C:
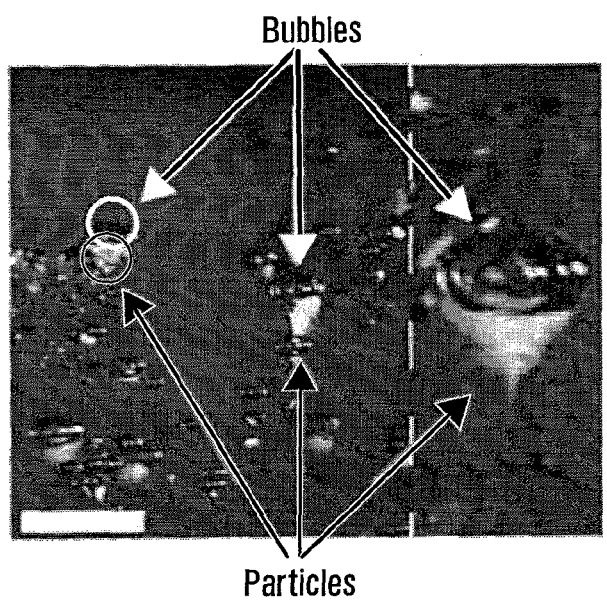
FIG. 2C is an image showing particles carried upward by $CO_2$ bubbles. Scale bars are 2 mm.

The rapid propulsion of particles in the vertical direction was attributed to $CO_2$ bubbles carrying the $CaCO_3$ particles upward as they reacted (FIG. 2C). When particles were clumped together into even larger and heavier aggregates, they tended to sink and propel with similar horizontal velocities of 3 mm/s. Large carbonate particles such as $Na_2CO_3$ particles of about 1 mm diameter were found to propel horizontally in 0.4 mm malic acid in water.

Figure 2D:
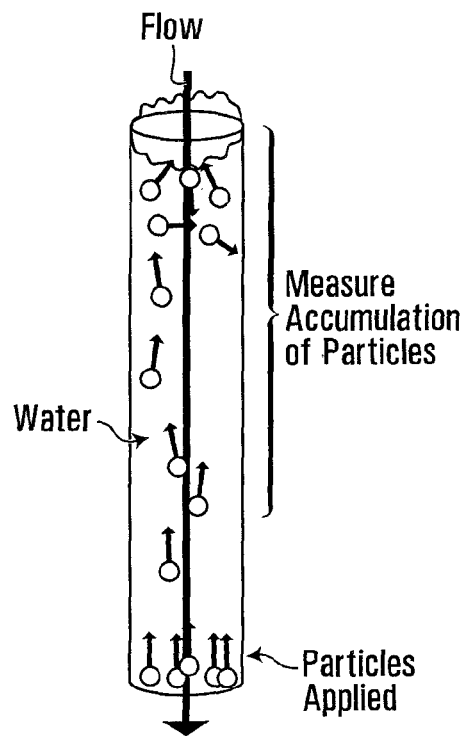
FIG. 2D is a schematic showing how propulsion through flowing solutions was measured. Particles were applied at the bottom of a tube and the movement of particles upstream though flowing water was quantified.
Figure 2E:
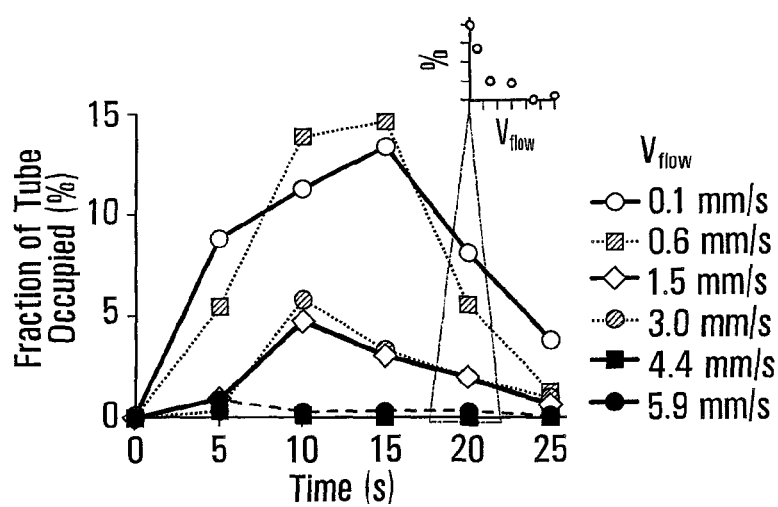
FIG. 2E is a graph showing that the amount of particles that propelled upstream decreased at higher flow rates. The inset shows the fraction of particles that accumulated for each flow velocity at 20 s.

To illustrate propulsion upstream through a flowing solution, $CaCO_3$ and TXA-$NH_3^+$, were mixed together and added to a solution flowing at speeds between 0.06 and 5.9 mm/s through a glass capillary (FIG. 2D). The aqueous solution of water contained 0.1% of a surfactant, to mimic surfactants in plasma, and had neutral pH. The particles were applied at the bottom of the tube and propelled upward. The area of the tube that filled with particles and bubbles was measured (FIG. 2E). Particles traveled through the capillary even when against flow velocities up to 3.0 mm/s. The amount of particles that entered the flowing solution decreased at higher flow velocities. Fluorescence images showed that fluorescently-labeled $CaCO_3$ particles traveled with the $CO_2$ bubbles and reached the top of the flowing solution. Using this approach, we have observed particles travelling up to about 1 meter upstream in the tubing.

The flow velocity of blood varies widely between different sized blood vessels and different types of wounds. In capillaries the flow velocity is approximately 1 mm/s, whereas in arteries with diameters of several millimeters, such as coronary arteries, the velocity is between 10 and 100 mm/s.[10] The $CaCO_3$ particles described above were capable of a velocity of 3 mm/s. While such a velocity would be insufficient to move against the flow of blood within an artery, such particles are capable of propulsion through blood flow in wounds and capillary beds.

In advanced clinical settings, intravascular catheters can sometimes be used to deliver agents to the vasculature feeding damaged vessels, and this approach is used to deliver embolic agents to halt blood flow. However treating severe bleeding from vessels that cannot be targeted with catheters, or when immediate treatment is necessary, requires more traditional approaches, such as topical compression. Compressing or packing materials into the area of bleeding is the standard treatment.[11] Many technologies and materials have been developed for this purpose, such as gelatin foams, modified cellulose and other functionalized dressings, and powders composed of zeolites. Thrombin can also be applied topically in solution. However, none of these methods are highly effective during severe bleeding or when external blood loss originates from inside a cavity of the body.

To create particles that affect blood clotting, thrombin (a serine protease that activates the coagulation system and directly cleaves fibrinogen) was adsorbed onto porous $CaCO_3$ particles prepared as described above. The carbonate microparticles were suspended at 10% w/v in 447 µM bovine thrombin (Thr) in 10 mM HEPES and incubated at 4° for 1 hr. The particles were purified by centrifugation (5 min at 10,000 g) to remove excess liquid, and were dried by lyophilization. We have also made porous $CaCO_3$ particles associated with the fibrolytic agent, uPA.

Figure 3A:
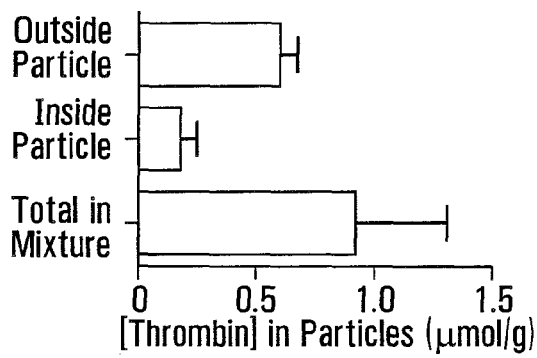
FIG. 3A is a graph showing amounts of thrombin adsorbed inside and outside of $CaCO_3$ particles.
Figure 3B:
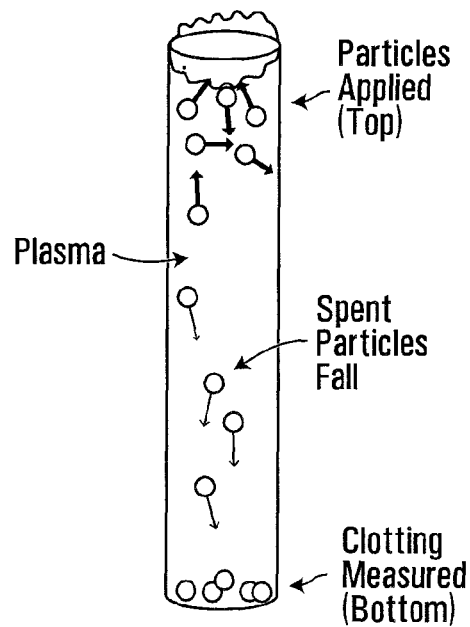
FIG. 3B is a schematic showing how clot time of non-flowing plasma was measured. Thrombin in a buffered solution or associated with $CaCO_3$ particles was placed near the top of a tube of non-flowing blood plasma. $CaCO_3$ particles were mixed with either protonated or unprotonated tranexamic acid, yielding propelling or non-propelling mixtures respectively.
Figure 3C:
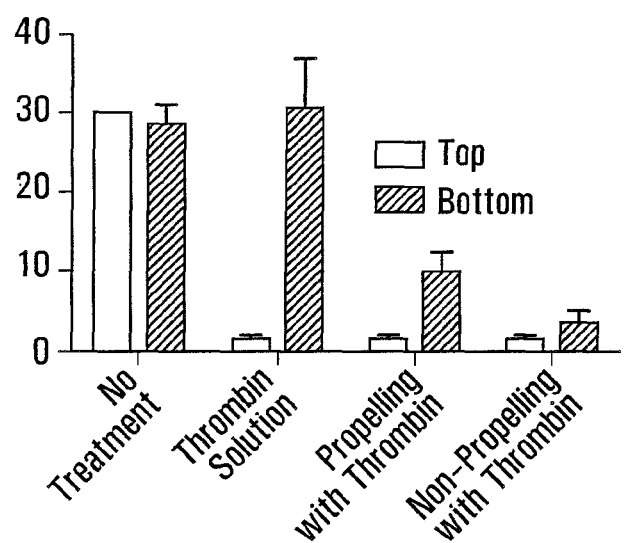
FIG. 3C is a graph showing clot initiation times at the tops and bottoms of tubes.

To determine the concentration of active Thr immobilized to the particles, we used a fluorescent thrombin substrate (Boc-Val-Pro-Arg-MCA, Peptide Institute Inc.), the cleavage of which by thrombin yields a blue fluorescent product detectable by spectrophotometry. To determine total thrombin content, the thrombin-calcium carbonate (Thr-$CaCO_3$) particles were solubilized in 100 mM HCl prior to addition of fluorescent substrate. To determine thrombin adsorbed within the pores of the microparticles, particles were washed with HEPES-buffered saline (HBS) prior to solubilization. To determine thrombin on the exterior of particles, particles were not solubilized prior to addition of fluorescent substrate. The unwashed particles contained 0.9 µmol of active thrombin per gram of $CaCO_3$, and after washing the particles with an aqueous solution, the particles retained 0.2 µmol/g (FIG. 3A). Approximately 0.6 µmol of active thrombin per gram of $CaCO_3$ was seen to be adsorbed to the particles. These particles rapidly clotted blood, both alone and when combined with TXA-$NH_3^+$ (FIG. 3B,C).

Thr-$CaCO_3$ was mixed at a 1:1 mass ratio with TXA-$NH_3^+$ to yield a propelling particle mixture. A non-propelling mixture consisted of a 1:1 ratio of Thr-$CaCO_3$ with lyophilized TXA-$NH_2$. The ability of the two mixtures to initiate clotting in platelet-poor blood plasma was measured and compared against addition of a similar amount of thrombin (approximately 1 pmol) in HEPES buffer and a control receiving no treatment.

As described above, $CaCO_3$ particles propel upward at a greater velocity than in a lateral direction. The ability of particles to clot both at the site of application and below the site was assessed by injecting particles near the top of a column of plasma that was 25 mm tall. Initiation of clotting was measured both at the top and the bottom of the column by monitoring the formation of fibrin. The blood plasma was laced with green-fluorescent beads in order to monitor movement and formation of solid fibrin mesh and clot initiation. Clotting at the top was measured visually, and when the plasma became opaque or appeared gelled, clotting was confirmed by gentle manipulation with a micropipette.

Both propelling and non-propelling particles immediately clotted plasma at the top of the column, which was detected within 2 min. The same response occurred when a solution containing an equivalent amount of dissolved thrombin was added. However, there were much larger differences in the clot times at the bottom of the columns of plasma between these samples.

Notably, the thrombin solution caused no acceleration of clot initiation at the bottom compared to the control. Clotting took about 30 min, as the clot needed to propagate down through the column by diffusion. Clotting at the bottom was faster using non-propelled particles, occurring in 3.7 min as compared to 10 min for the propelled particles. However, this enhanced downward clotting rate was due to the unreacted thrombin-loaded $CaCO_3$ particles sinking to the bottom. Most propelled particles reacted and produced gas at the top so only a fraction of the particles sank to the bottom yielding a slightly slower clot time compared to non-propelling particles. Although the propelled particles outperformed the thrombin solution in this assay, a particular advantage for the propelling particles would come from an ability to propel though flowing solutions.

Figure 3D:
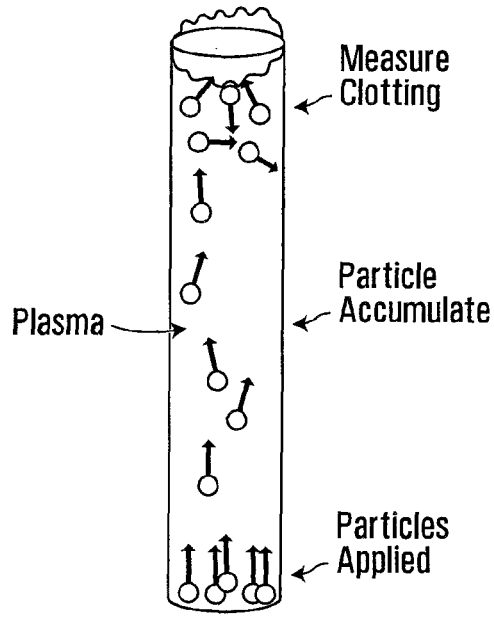
FIG. 3D is a schematic of clotting and occlusion of flowing blood plasma, showing flow rate of plasma being measured after particles were applied at the bottom of a tube.
Figure 3E:
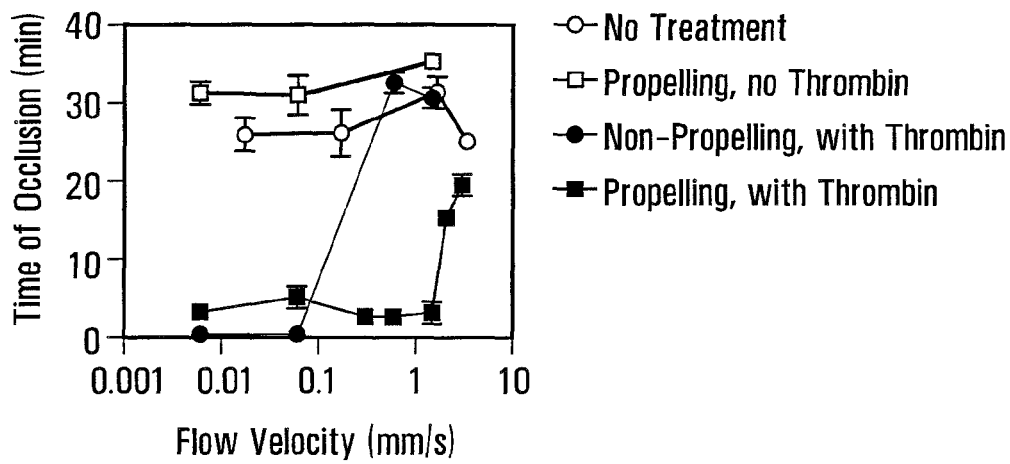
FIG. 3E is a graph showing clotting of plasma at various flow rates by thrombin-loaded particles. $P<$*0.05, 0.01, *0.001. n=3. Error bars indicate S.E.M.

To show propelling thrombin particles clotting flowing plasma, particles were applied to the bottom of plasma flowing through a glass capillary tube (FIG. 3D,E). A microfluidic system was used to control the flow of plasma, and monitor the flow to determine when clotting occluded flow in the capillary tube. At flow velocities between 0.006 and 3.4 mm/s, the background occlusion times in the system were approximately 30 min. When no treatment was applied, or when propelled particles that did not contain thrombin were applied, occlusion also occurred at approximately 30 min. The thrombin alone occluded at very slow velocities of up to 0.06 mm/s, and showed no difference from controls at 0.6 mm/s. The non-propelled thrombin was able to form a clot at the exit of the tubing, but only at low flows was this clot able to persist and propagate up the tubing. At high flows, the clot was easily pushed out and the flow of plasma resumed. The propelled thrombin initiated clotting and occluded flow at velocities much higher than non-propelled thrombin. The particles propelled upwards, against flow, and accumulated high within the tubing. Clotting was seen to initiate at regions with the highest concentration of particles. At a flow velocity of 3 mm/s, the time of occlusion was still considerably faster than the non-propelled mixture or controls. This shows that the self-propelling particles loaded with thrombin would be effective at clotting flowing plasma by initiating clotting upstream of the site of application.

Figure 4A:
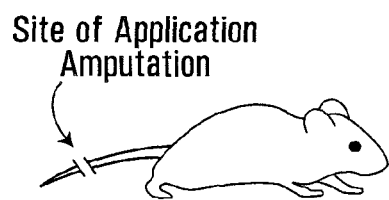
FIG. 4A is a perspective view of a mouse used in a model for severe hemorrhage. A terminal 8 mm portion of the mouse tail was amputated.
Figure 4B:
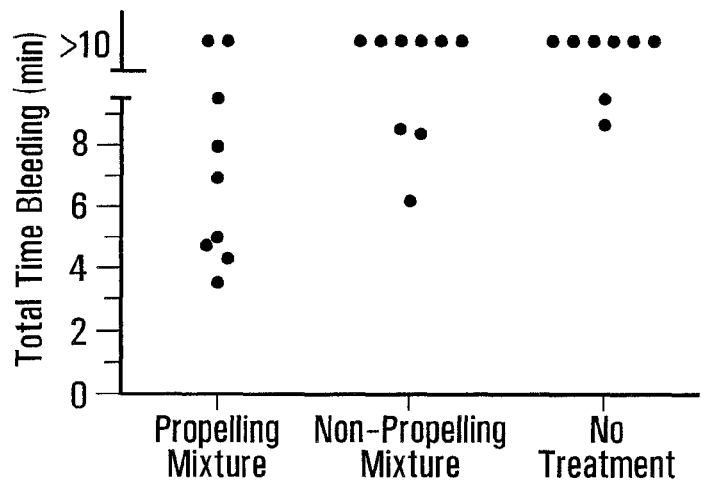
FIG. 4B is a graph showing total bleeding times following application of propelled and non-propelled thrombin associated particles at the site of amputation. Mice were observed for 10 min following amputation. *p<0.05.

Ability of the self-propelling particles to halt bleeding in a mouse model of hemorrhage was also tested. Mouse tails were amputated 8 mm from the tip to achieve severe hemorrhage (FIG. 4A). To the site of amputation, 20 mg of either propelling or non-propelling thrombin-loaded particles were applied for 30 sec. Control mice received no treatment following amputation. After application, tails were immersed in warm phosphate-buffered saline (PBS) that contained citrate, and bleeding was monitored for 10 min. The experiment concluded after 10 min to ensure the death of the mouse was not an endpoint. The propelled thrombin significantly decreased the bleeding time compared to both other groups (FIG. 4B). In 7 out of 9 mice (78%) that received that propelled mixture, bleeding stopped during observation. In contrast, without propulsion, only 3 out of 9 mice (33%) and 2 out of 8 mice (25%) stopped bleeding in the groups receiving non-propelled thrombin and no treatment, respectively. Fluorescent labelled particles were also employed to determine distance of travel within the mouse tail. FITC-dextran labelled particles were located up to 10 mm upstream in the tail, whereas $CaCO_3$ particles carried labelled cargo particles (0.2 µm diameter fluorescent polystyrene beads) up to 4 mm upstream in the tail. Also, there was no increase in inflammation in the mice treated with the self-propelled particles 3 days post-procedure. These results demonstrate use of this embodiment as a local or topically applied procoagulant in vivo.

Figure 5:
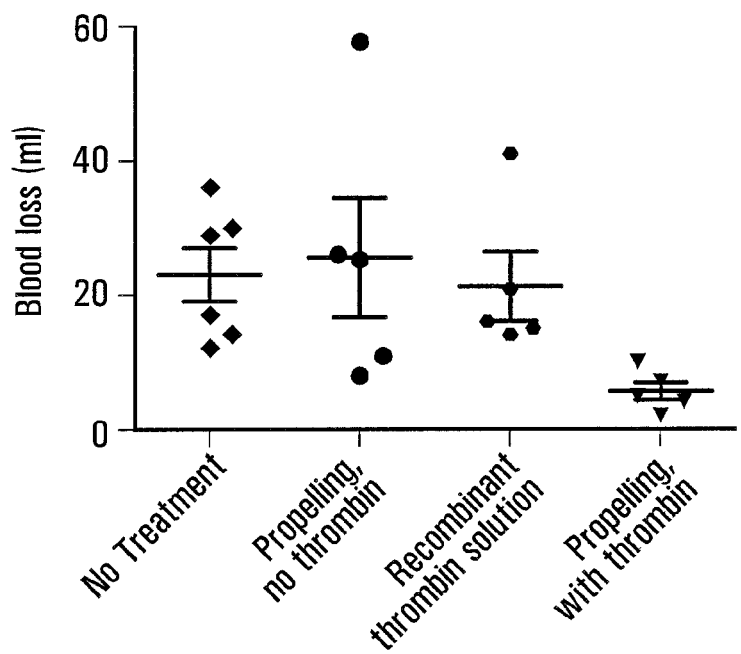
FIG. 5 is a graph showing volumes of blood lost from mice after their livers were punctured. *P<0.05, **P<0.01. Error bars indicate S.E.M.

We also employed a mouse model to quantify blood loss from a hemorrhage resulting from liver puncture. Blood loss following liver puncture was quantified by collecting blood into pre-weighed filter papers of approximately 2 cm by 2 cm, arranged to line the site of puncture, which were compared to control papers pre-soaked with known volumes of fresh blood. We found that total blood loss was significantly decreased by application of Thr-CaCO$_3$ particles with TXA-NH$_3^+$, as compared to no treatment or application of the particles without associated thrombin. Furthermore, there was a significant reduction in blood loss when the Thr-CaCO$_3$ particles were employed, as compared to application of a solution of recombinant thrombin (FIG. 5). In addition, we found that intravenous administration of the CaCO$_3$ microparticles or a reacted mixture of the microparticles with TXA-NH$_3^+$ to mice resulted in no significant sign of liver toxicity or pulmonary embolism in the mice three days after injection, as compared to injection of saline. This was determined by measuring serum levels of alanine aminotransferase and asparate aminotransferase as well as histological examination of H & E-stained and Masson's trichrome-stained lung sections.

Although the foregoing invention has been described in some detail by way of illustration and example for purposes of clarity of understanding, it will be readily apparent to those of skill in the art in light of the teachings of this invention that changes and modification may be made thereto without departing from the spirit and scope of the invention. All patents, patent applications and published documents referred to herein are hereby incorporated by reference.

REFERENCES

1. Paxton, W. F., Sundararajan, S., Mallouk, T. E. & Sen, A. Chemical locomotion. *Angewandte Chemie-International Edition* 45, 5420-5429 (2006).
2. Zhao, G., Viehrig, M. & Pumera, M. Challenges of the movement of catalytic micromotors in blood. *Lab on a Chip* 13, 1930-1936 (2013).
3. Wu, Z. et al. Self-Propelled Polymer-Based Multilayer Nanorockets for Transportation and Drug Release. *Angewandte Chemie-International Edition* 52, 7000-7003 (2013).
4. Patra, D. et al. Intelligent, self-powered, drug delivery systems. *Nanoscale* 5, 1273-1283 (2013).
5. Kuralay, F. et al. Self-Propelled Carbohydrate-Sensitive Microtransporters with Built-In Boronic Acid Recognition for Isolating Sugars and Cells. *Journal of the American Chemical Society* 134, 15217-15220 (2012).
6. Ismagilov, R. F., Schwartz, A., Bowden, N. & Whitesides, G. M. Autonomous movement and self-assembly. *Angewandte Chemie-International Edition* 41, 652-654 (2002).
7. Garcia-Gradilla, V. et al. Functionalized ultrasound-propelled magnetically guided nanomotors: toward practical biomedical applications. *ACS nano* 7, 9232-9240 (2013).
8. Dreyfus, R. et al. Microscopic artificial swimmers. *Nature* 437, 862-865 (2005).
9. Volodkin, D. V., Larionova, N. I. & Sukhorukov, G. B. Protein encapsulation via porous CaCO3 microparticles templating. *Biomacromolecules* 5, 1962-1972 (2004).
10. Vennemann, P., Lindken, R. & Westerweel, J. In vivo whole-field blood velocity measurement techniques. *Experiments in Fluids* 42, 495-511 (2007).
11. Kozen, B. G., Kircher, S. J., Henao, J., Godinez, F. S. & Johnson, A. S. An alternative hemostatic dressing: Comparison of CELOX, HemCon, and QuikClot. *Academic Emergency Medicine* 15, 74-8 (2008).
12. Gao, W., et al., Hydrogen-Bubble-Propelled Zinc-Based Microrockets in Strongly Acidic Media. *J. Am. Chem. Soc.* 134:897-900 (2012).
13. Kawai, K., et al., Calcium-Based Nanoparticles Accelerate Skin Wound Healing. *PLoS ONE* 6(11):e27106 (2011).
14. Chow, K. T., et al., Formulation of Hydrophilic Non-Aqueous Gel: Drug Stability in Different Solvents and Rheological Behavior of Gel Matrices, *Pharmaceutical Research* 25(1):207-217 (2008).

The invention claimed is:

1. A non-aqueous composition, comprising:
   (a) carbonate salt particles; and
   (b) an organic acid in solid form, wherein the organic acid is selected from the group consisting of doubly-protonated tranexamic acid (TXA-NH$_3^+$), aminocaproic acid, and mixtures thereof;
   wherein the carbonate salt particles and organic acid in solid form are present in the composition in the form of a powder or granules in an amount effective to propel the carbonate particles and organic acid in solid form through an aqueous fluid when the non-aqueous composition is introduced to an aqueous fluid.

2. The non-aqueous composition of claim 1, wherein the carbonate salt particles are calcium carbonate particles.

3. The non-aqueous composition of claim 1 further comprising a biologically active agent.

4. The non-aqueous composition of claim 3, wherein the biologically active agent affects clotting, promotes clotting, or diminishes clots or clotting.

5. The non-aqueous composition of claim 3, wherein the biologically active agent is thrombin.

6. The non-aqueous composition of claim 1, present in a capsule, in tablet form, in or on a microcarrier, in or on a non-aqueous carrier, on or within the material of a gauze, a wound dressing, an instrument for cleaning wounds, a balloon for surgical application, a sponge, or a nasal packing material, or within or on a delivery device.

7. A wound dressing, comprising the composition of claim 1.

8. The wound dressing of claim 7, wherein the wound dressing is a gauze.

9. A method of conveying a cargo molecule or cargo particle through an aqueous fluid, the method comprising introducing the non-aqueous composition of claim 1 and a cargo molecule or cargo particle into the fluid whereupon carbon dioxide bubbles are released from the composition propels the carbonate salt particles and the organic acid in solid form through the fluid.

10. The method of claim 9, wherein the cargo molecule or cargo particle is a biologically active agent.

11. The method of claim 10, wherein the biologically active agent affects clotting, promotes clotting, or diminishes clots or clotting.

12. The method of claim 10, wherein the biologically active agent is thrombin.

13. The method of claim 9, wherein the fluid is a biological fluid.

14. The method of claim 9, wherein the fluid is blood.

15. The method of claim 9, wherein the composition is introduced in vivo.

\* \* \* \* \*